(12) United States Patent
Yuan et al.

(10) Patent No.: US 11,774,422 B2
(45) Date of Patent: Oct. 3, 2023

(54) SELECTIVE MULTI-GAS DETECTION THROUGH PULSE HEATING IN A GAS SENSOR

(71) Applicant: STMicroelectronics PTE LTD, Singapore (SG)

(72) Inventors: Fangxing Yuan, Singapore (SG); Ravi Shankar, Singapore (SG); Olivier Le Neel, Singapore (SG)

(73) Assignee: STMicroelectronics PTE LTD, Singapore (SG)

( * ) Notice: Subject to any disclaimer, the term of this patent is extended or adjusted under 35 U.S.C. 154(b) by 813 days.

(21) Appl. No.: 16/458,561

(22) Filed: Jul. 1, 2019

(65) Prior Publication Data
US 2020/0033309 A1 Jan. 30, 2020

Related U.S. Application Data

(60) Provisional application No. 62/703,195, filed on Jul. 25, 2018.

(51) Int. Cl.
*G01N 33/00* (2006.01)
*G01N 29/22* (2006.01)

(52) U.S. Cl.
CPC ........ *G01N 33/0013* (2013.01); *G01N 29/228* (2013.01); *G01N 33/0016* (2013.01); *G01N 33/0031* (2013.01)

(58) Field of Classification Search
CPC .... G01N 33/00; G01N 29/22; G01N 33/0013; G01N 29/228; G01N 33/0016; G01N 33/0031

(Continued)

(56) References Cited

U.S. PATENT DOCUMENTS 4,457,161 A * 7/1984 Iwanaga ................ G01N 27/12
340/634
4,847,783 A * 7/1989 Grace .................. G01N 27/123
422/98

(Continued)

FOREIGN PATENT DOCUMENTS

CN 103718031 A 4/2014
CN 107632113 A 1/2018

(Continued)

OTHER PUBLICATIONS

Chesler et al., "Nanostructured $SnO_2$—ZnO composite gas sensors for selective detection of carbon monoxide," *Beilstein Journal of Nanotechnology* 7:2045-2056, 2016.

(Continued)

*Primary Examiner* — Peter J Macchiarolo
*Assistant Examiner* — Mohammed E Keramet-Amircolai
(74) *Attorney, Agent, or Firm* — SEED IP LAW GROUP LLP

(57) ABSTRACT

The present disclosure is directed to a selective multi-gas sensor device that detects when a high concentration level of a particular gas, such as methane, carbon monoxide, and/or ethanol, is present. The selective multi-gas sensor device detects and identifies a particular gas based on a ratio between a sensitivity of a gas sensitive material at a first temperature and a sensitivity of the gas sensitive material at a second temperature.

19 Claims, 5 Drawing Sheets

(58) Field of Classification Search
USPC .......................................................... 73/23.2
See application file for complete search history.

(56) References Cited

U.S. PATENT DOCUMENTS

| | | | | | |
|---|---|---|---|---|---|
| 5,621,162 | A | * | 4/1997 | Yun | G01N 27/125 |
| | | | | | 73/31.06 |
| 5,879,631 | A | * | 3/1999 | Wewers | G01N 33/0014 |
| | | | | | 422/83 |
| 6,070,450 | A | * | 6/2000 | Takao | G01N 33/004 |
| | | | | | 73/23.31 |
| 2004/0099045 | A1 | * | 5/2004 | Demarest | C25B 15/08 |
| | | | | | 73/23.2 |
| 2007/0220954 | A1 | * | 9/2007 | Fleischer | G01N 27/4143 |
| | | | | | 73/31.05 |
| 2007/0266858 | A1 | * | 11/2007 | Alm | G01N 30/463 |
| | | | | | 96/105 |
| 2009/0090626 | A1 | * | 4/2009 | Holt | H01M 8/04216 |
| | | | | | 436/2 |
| 2013/0046485 | A1 | * | 2/2013 | Norman | G01N 33/0031 |
| | | | | | 702/24 |
| 2014/0154811 | A1 | * | 6/2014 | Sjong | G01N 27/40 |
| | | | | | 436/72 |
| 2014/0208828 | A1 | * | 7/2014 | Von Waldkirch | G01N 27/123 |
| | | | | | 73/25.05 |
| 2016/0018356 | A1 | | 1/2016 | Shankar et al. | |
| 2016/0161542 | A1 | * | 6/2016 | Higuchi | H05B 1/0227 |
| | | | | | 324/750.01 |
| 2018/0313800 | A1 | * | 11/2018 | Rogers | G01N 33/0016 |

FOREIGN PATENT DOCUMENTS

| | | |
|---|---|---|
| CN | 210803349 U | 6/2020 |
| GB | 1448307 A | 9/1976 |
| JP | H07198644 A | 8/1995 |
| JP | 2006023256 A | 1/2006 |
| JP | 2010066009 A | 3/2010 |
| JP | 2017009472 A | 1/2017 |

OTHER PUBLICATIONS

Majeri et al., "Approach for power reduction using pulse on chemical gas sensor," *Sensors, Energy Harvesting, Wireless Network & Smart Objects Conference 2017*, Gardanne / Aix en Provence, France, Nov. 15-17, 2017, 15 pages.

Majeri et al., "Pulsed Mode for Power Reduction Micro Gas Sensor," *Sensors, Energy Harvesting, Wireless Network & Smart Objects Conference 2017*, Gardanne / Aix en Provence, France, Nov. 15-17, 2017, 3 pages.

Umar et al. (Ed.), *Metal Oxide Nanostructures and Their Applications*, American Scientific Publishers, Valencia, California, 2010, Chapter 2, Bochenkov et al., "Sensitivity, Selectivity, and Stability of Gas-Sensitive Metal-Oxide Nanostructures," pp. 31-52 (24 pages).

* cited by examiner

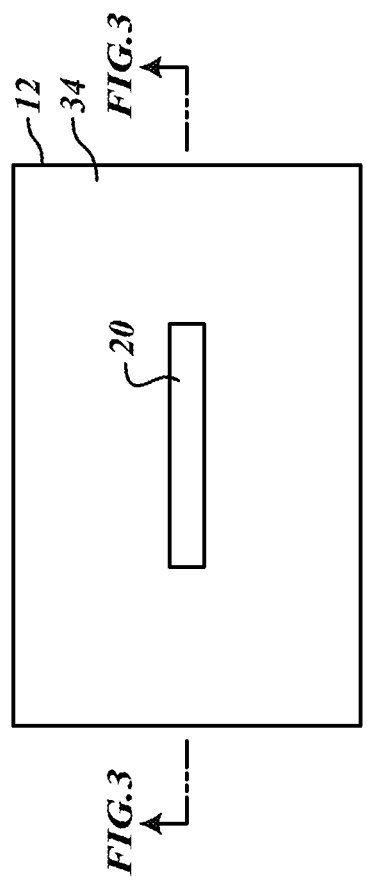
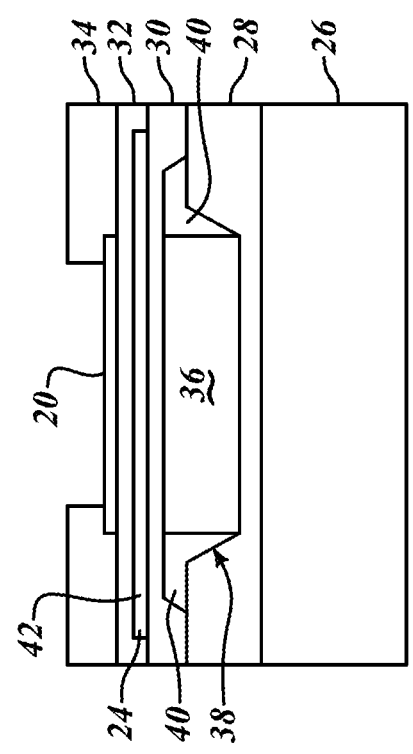

SELECTIVE MULTI-GAS DETECTION THROUGH PULSE HEATING IN A GAS SENSOR

BACKGROUND

Technical Field

The present disclosure is directed to a selective multi-gas sensor device and method for selectively detecting multiple gases using the selective multi-gas sensor device.

Description of the Related Art

Good air quality is important to maintain one's health, as air pollution may lead to a variety of health issues, such as cardiopulmonary ailments. Unfortunately, air pollution is not limited to outdoor pollution. A large range of chemical compounds can be found in indoor environments. For example, large concentrations of methane, carbon monoxide, and ethanol are often detected in homes, offices, and factories. Consequently, homes, offices, and factories are often equipped with gas sensors to detect harmful levels of gases and alert users of possible gas leakages.

Most gas sensors are designed to detect a single species of gas. For example, a current gas sensor is often configured to detect one of methane, carbon monoxide, and ethanol. In order to detect multiple different gases, multiple gas sensors are included in a single device. For instance, in order to detect carbon monoxide and ethanol, a gas sensor that detects carbon monoxide and another gas sensor that detects ethanol will be included in a single device. Including multiple gas sensors in a single device, however, leads to large power consumption.

BRIEF SUMMARY

The present disclosure is directed to a selective multi-gas sensor device. The selective multi-gas sensor device is configured to identify a particular gas and detect when a high concentration level of the gas is present. For example, in one embodiment, the selective multi-gas sensor device is configured to detect when a high concentration level of methane, carbon monoxide, and/or ethanol is present.

The selective multi-gas sensor device includes a gas sensor, a resistance measurement circuit, a power source, and a controller. The gas sensor is an active sensor that detects gases. The gas sensor includes a gas sensitive material that chemically reacts with gases, a temperature sensor that measures a current temperature of the gas sensitive material, and a heater that heats the gas sensitive material. The resistance measurement circuit measures a resistance of the gas sensitive material; and the power source supplies a heating signal to turn the heater on and heat the gas sensitive material. The controller is configured to obtain a current temperature of the gas sensitive material measured by the temperature sensor, obtain a resistance of the gas sensitive material measured by the resistance measurement circuit, and instruct the power source to supply a heating signal to power the heater to heat the gas sensitive material.

The selective multi-gas sensor device identifies and detects a particular gas based on a ratio between a sensitivity of the gas sensitive material when the heater is turned on and a sensitivity of the gas sensitive material when the heater is turned off. In particular, the selective multi-gas sensor device heats the gas sensitive material using a pulse voltage signal to power the heater. The selective multi-gas sensor device measures a first resistance of the gas sensitive material when the pulse voltage signal has a low voltage level (i.e., when the heater is off), and calculates a first sensitivity level of the gas sensitive material based on the first resistance. The selective multi-gas sensor device also measures a second resistance of the gas sensitive material when the pulse voltage signal has a high voltage level (i.e., when the heater is on), and calculates a second sensitivity level of the gas sensitive material based on the second resistance. The selective multi-gas sensor device then detects and identifies a gas based on a ratio between the first sensitivity level and the second sensitivity level.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

FIG. 2 is a top view of a gas sensor according to an embodiment of the present disclosure.

FIG. 3 is a cross-sectional view of a gas sensor along the axis shown in FIG. 2 according to an embodiment of the present disclosure.

DETAILED DESCRIPTION

In the following description, certain specific details are set forth in order to provide a thorough understanding of various aspects of the disclosed subject matter. However, the disclosed subject matter may be practiced without these specific details. In some instances, well-known structures and methods of manufacturing electronic devices and gas sensors have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting or glass substrates, whether or not the components are coupled together into a circuit or able to be interconnected. Throughout the specification, the term "layer" is used in its broadest sense to include a thin film, a cap, or the like, and one layer may be composed of multiple sub-layers.

The present disclosure is directed to a selective multi-gas sensor device, and a method for selectively detecting multiple gases using the selective multi-gas sensor device.

Figure 1:
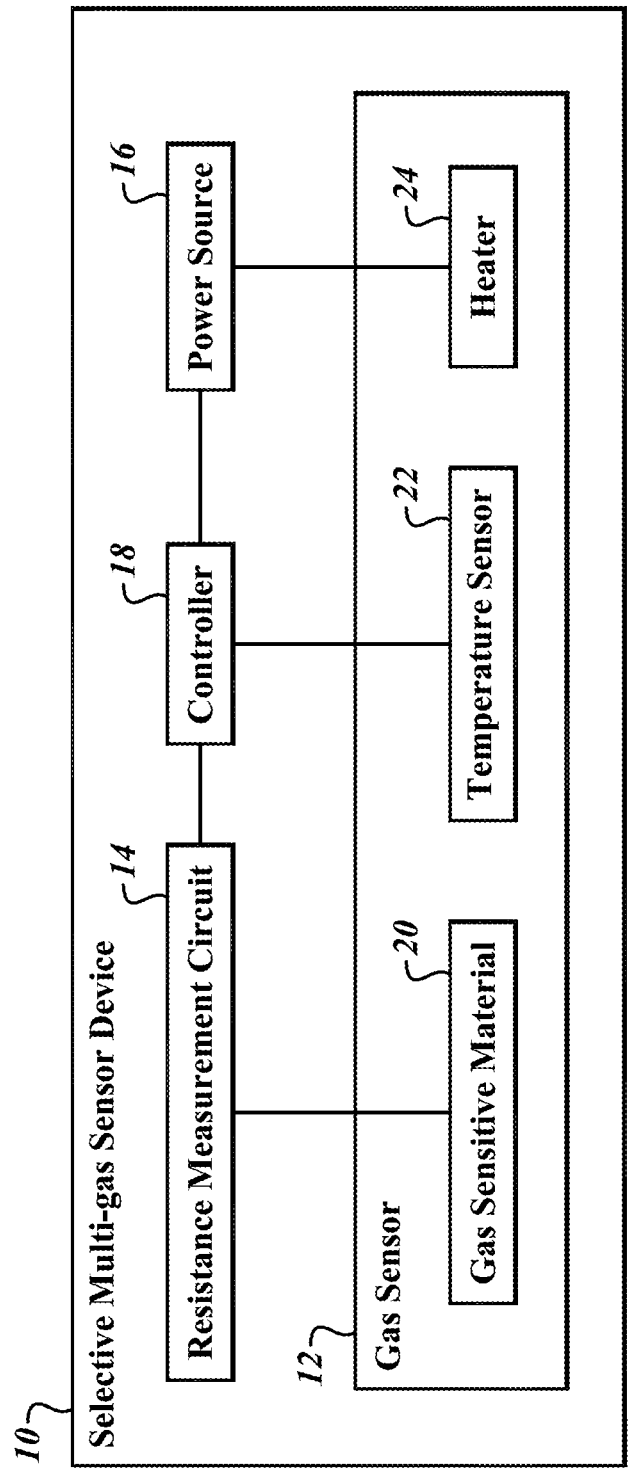
FIG. 1 is a block diagram of a selective multi-gas sensor device according to an embodiment of the present disclosure.

FIG. 1 is a block diagram of a selective multi-gas sensor device 10 according to an embodiment of the present disclosure. The selective multi-gas sensor device 10 is configured to selectively detect multiple different gases. Stated differently, the selective multi-gas sensor device 10 is able to individually detect when a high concentration level of a particular gas out of a plurality of gases is present. For example, in one embodiment, the selective multi-gas sensor device 10 is configured to detect when a high concentration level of methane, carbon monoxide, and/or ethanol is present. The selective multi-gas sensor device 10 includes a gas sensor 12, a resistance measurement circuit 14, a power source 16, and a controller 18.

The gas sensor 12 is an active sensor that detects gases. The gas sensor 12 includes a gas sensitive material 20, a temperature sensor 22, and a heater 24.

The gas sensitive material 20 is an active sensor area. The gas sensitive material 20 is made of a material that chemically reacts with gases, such as methane, carbon monoxide, and ethanol.

In one embodiment, the gas sensitive material 20 is a semiconductor metal oxide (SMO) film that includes, for example, tin dioxide, zinc oxide, and/or indium oxide. When an SMO film is heated to certain temperatures, the SMO film will react with one or more gases through an oxidation or reduction process. The exchange of electrons with the gas reactant results in overall resistance changes in the SMO film. For example, when an SMO film that includes tin dioxide is heated to approximately 300 degrees Celsius, a resistance of the SMO film will change in the presence of carbon monoxide and/or ethanol. As a result, a presence of a gas may be detected by monitoring a current resistance or conductivity of the SMO film. It is noted that, although SMO films are referred to throughout this disclosure, other gas sensitive materials may be used.

In one embodiment, the gas sensitive material 20 is a thin film. For example, in one embodiment, the gas sensitive material 20 is a thin SMO film that is between 50 nanometers and 150 nanometers thick. As will be discussed in further detail below, using a thin film for the gas sensitive material 20 allows the gas sensitive material 20 to be able to rapidly heat to a target temperature, as compared to a gas sensor with a gas sensitive material made of a thick film (e.g., between 5 micrometers and 20 micrometers thick). As a result, gas detection may be performed faster and power consumption may be decreased.

The temperature sensor 22 measures a current temperature of the gas sensitive material 20. The temperature sensor 22 is positioned adjacent to the gas sensitive material 20 in order to obtain accurate measurements. As will be discussed in further detail below, in one embodiment, the temperature sensor 22 is used as a feedback loop for adjusting the heater 24 to heat the gas sensitive material 20 to a desired temperature.

The heater 24 heats the gas sensitive material 20. The heater 24 is positioned adjacent to the gas sensitive material 20 in order to heat the gas sensitive material 20 rapidly. As will be discussed in further detail below, in one embodiment, the heater 24 is used to alternate a temperature of the gas sensitive material 20 between a first temperature and a second temperature.

In one embodiment, the heater 24 is a resistive heater. Namely, the heater 24 is heated by the Joule effect and heats the gas sensitive material 20 by radiant heat. It is noted, however, other types of heaters may be used.

The resistance measurement circuit 14 measures a resistance of the gas sensitive material 20. As will be discussed in further detail below, in one embodiment, resistances measured by the resistance measurement circuit 14 are used to measure sensitivity levels of the gas sensitive material 20 and detect a presence of a gas.

In one embodiment, the resistance measurement circuit 14 is a voltage divider circuit that includes the gas sensitive material 20. For example, the resistance measurement circuit 14 may include a resistor (with a known resistance) having a first end coupled to a voltage source (with a known voltage level) and a second end coupled to the gas sensitive material 20. The resistance of the gas sensitive material 20 may then be determined based on the resistance of the resistor, the voltage level of the voltage source, and a measured voltage at the second end of the resistor (i.e., where the resistor and the gas sensitive material 20 are connected). It is noted, however, other types of resistance measurement circuits may be used.

The power source 16 supplies heating signal (i.e., a power signal, such as a voltage or current signal) to power the heater 24 which, in turn, heats the gas sensitive material 20. In one embodiment, the heat provided by the heater 24 is proportional to the heating signal received from the power source 16. For example, the heater 24 will heat the gas sensitive material 20 to a high temperature (e.g., 300 degrees Celsius) when the heater 24 receives a high voltage level (e.g., 1.2 volts) from the power source 16. Conversely, the heater 24 will no longer heat the gas sensitive material 20 when the heater 24 receives a zero voltage level (e.g., 0 volts) from the power source 16. As will be discussed in further detail below, in one embodiment, the heating signal supplied by the power source 16 is a pulse voltage signal that alternates between high and low voltage levels to the heater 24.

The controller 18 controls the selective multi-gas sensor device 10. The controller 18 is coupled to and controls the gas sensor 12, the resistance measurement circuit 14, and the power source 16. In one embodiment, the controller 18 is configured to obtain a current temperature of the gas sensitive material 20 measured by the temperature sensor 22, obtain a current resistance of the gas sensitive material 20 measured by the resistance measurement circuit 14, and instruct the power source 16 to supply a heating signal to power the heater 24 to heat the gas sensitive material 20. As will be discussed in further detail below, in one embodiment, the controller 18 controls the selective multi-gas sensor device 10, specifically the gas sensor 12, the resistance measurement circuit 14, and the power source 16, to selectively detect multiple different gases.

The controller 18 may be any type of controller, processor, or application specific integrated circuit (ASIC) that, for example, communicates with the resistance measurement circuit 14 and the temperature sensor 22, and controls the power source 16.

The gas sensor 12, the resistance measurement circuit 14, the power source 16, and the controller 18 may be fabricated in the same package, in separate chips in separate packages, or separate chips in a single package. For example, in one embodiment, the gas sensor 12, the resistance measurement circuit 14, the power source 16, and the controller 18 are within a single package or fabricated in a single semiconductor substrate. In another embodiment, the gas sensor 12, the resistance measurement circuit 14, the power source 16, and the controller 18 are in respective packages.

FIG. 2 is a top view of the gas sensor 12 according to an embodiment of the present disclosure. FIG. 3 is a cross-sectional view of the gas sensor along the axis shown in FIG. 2 according to an embodiment of the present disclosure. It is beneficial to review FIGS. 2 and 3 together. It is noted that the dimensions set forth herein are provided as examples. Other dimensions are envisioned for this embodiment and all other embodiments of this application.

The gas sensor 12 includes the gas sensitive material 20; the heater 24; a substrate 26; a first insulating layer 28; a second insulating layer 30; a third insulating layer 32; and a fourth insulating layer 34.

The substrate 26 provides a support for the various components of the gas sensor 12. In one embodiment, the substrate 26 is made of silicon or glass. In one embodiment, the substrate 26 has a thickness in the range of 500 micrometers to 600 micrometers.

The first insulating layer 28 is formed on the substrate 26 using, for example, deposition or a growth process. In one embodiment, the first insulating layer 28 is made of a dielectric material, such as oxide or silicon nitride. In one embodiment, the first insulating layer 28 has a thickness in the range of 3 micrometers to 10 micrometers.

The second insulating layer 30 is formed on the first insulating layer 28 using, for example, deposition or a growth process. In one embodiment, the second insulating layer 30 is made of a dielectric material, such as oxide or silicon nitride. In one embodiment, the second insulating layer 30 has a thickness in the range of 300 nanometers to 550 nanometers.

A cavity 36 is formed between the first insulating layer 28 and the second insulating layer 30. The cavity 36 provides an air gap between the first insulating layer 28 and the second insulating layer 30. As air has low thermal conductivity, the cavity 36 provides thermal insulation and confines heat within the gas sensor 12. As a result, a temperature of the gas sensitive material 20 may be maintained with less power.

In one embodiment, the cavity 36 is formed by patterning a recess 38 in the first insulating layer 28 using, for example, photolithography and etching techniques; and filling the recess 38 with a sacrificial material 40. In one embodiment, the sacrificial material 40 is made of polyimide. As polyimide has low thermal conductivity, using polyimide for the sacrificial material 40 provides additional thermal insulation for the gas sensor 12. The second insulating layer 30 is then formed on the first insulating layer 28 and the sacrificial material 40. Portions of the sacrificial material 40 are then removed using, for example, photolithography and etching techniques. As best shown in FIG. 3, remaining portions of the sacrificial material 40 provide additional support for portions of the second insulating layer 30 overlying the cavity 36. In one embodiment, the cavity 36 has a depth in the range of 2 micrometers to 5 micrometers.

The heater 24 is formed on the second insulating layer 30 using, for example, deposition. The heater 24 directly overlies the cavity 36. As previously discussed, in one embodiment, the heater 24 is a resistive heater that is heated by the Joule effect and heats the gas sensitive material 20 by radiant heat. In this embodiment, the heater 24 includes a resistive layer 42 made of a conductive material, such as tantalum aluminum. In one embodiment, the resistive layer 42 has a thickness in the range of 100 nanometers to 200 nanometers. Although a single resistive layer is shown in FIG. 3, the heater 24 may include a plurality of resistive layers.

The third insulating layer 32 is formed on the second insulating layer 30 and the heater 24 using, for example, deposition or a growth process. In one embodiment, the third insulating layer 32 is made of a dielectric material, such as oxide or silicon nitride. In one embodiment, the third insulating layer 32 has a thickness in the range of 200 nanometers to 400 nanometers.

The gas sensitive material 20 is formed on the third insulating layer 32 using, for example, deposition. The gas sensitive material 20 may be formed by forming a gas sensitive layer on the third insulating layer 32 and patterning the gas sensitive layer using, for example, photolithography and etching techniques. As previously discussed, in one embodiment, the gas sensitive material 20 is an SMO that chemically reacts with various gases in a surrounding environment. For example, the gas sensitive material may include tin dioxide, zinc oxide, and/or indium oxide.

The fourth insulating layer 34 is formed on the third insulating layer 32 and the gas sensitive material 20 using, for example, deposition or a growth process. The fourth insulating layer 34 is patterned using, for example, photolithography and etching techniques to expose the gas sensitive material 20 to a surrounding environment. In one embodiment, the fourth insulating layer 34 is made of a dielectric material, such as silicon oxide or silicon nitride. In one embodiment, the fourth insulating layer 34 has a thickness in the range of 300 nanometers to 550 nanometers.

As previously discussed, in one embodiment, the gas sensor 12 is formed on the same substrate as the resistance measurement circuit 14, the controller 18, and the power source 16. In another embodiment, the resistance measurement circuit 14, the controller 18, and the power source 16 are formed on a separate substrate from the gas sensor 12, and are electrically coupled to the gas sensor 12 via an interconnect.

It is noted that the temperature sensor 22 is not shown in FIGS. 2 and 3 for simplicity purposes. As previously discussed, in one embodiment, the temperature sensor 22 is positioned adjacent to the gas sensitive material 20 in order to obtain accurate measurements.

Although not shown in FIGS. 2 and 3, the selective multi-gas sensor device 10 may include a plurality of conductive layers that electrically couple the gas sensor 12, including the gas sensitive material 20, the temperature sensor 22, and the heater 24; the resistance measurement circuit 14; the power source 16; and the controller 18 to each other and/or other electrical components (e.g., transistors, capacitors, resistors, etc.).

Figure 4:
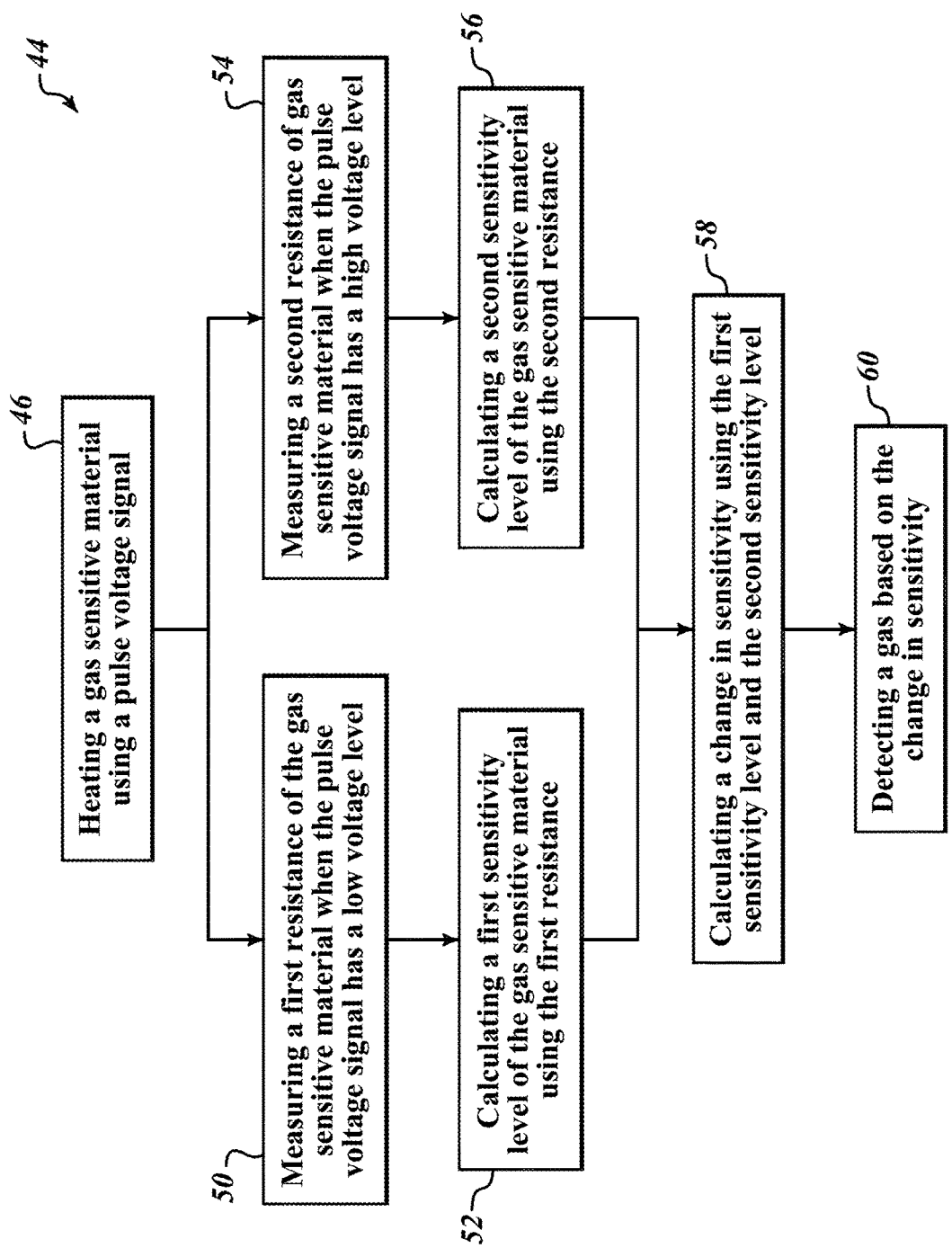
FIG. 4 is a flow diagram of a method of operating a selective multi-gas sensor device to selectively detect a gas according to an embodiment of the present disclosure.

FIG. 4 is a flow diagram of a method 44 of operating the selective multi-gas sensor device 10 to selectively detect a gas according to an embodiment of the present disclosure.

In block 46, the selective multi-gas sensor device 10 heats the gas sensitive material 20 using a pulse voltage signal. Namely, the controller 18 instructs the power source 16 to generate and apply the pulse voltage signal to the heater 24. The heater 24 receives the pulse voltage signal and heats the gas sensitive material 20 in response.

Figure 5:
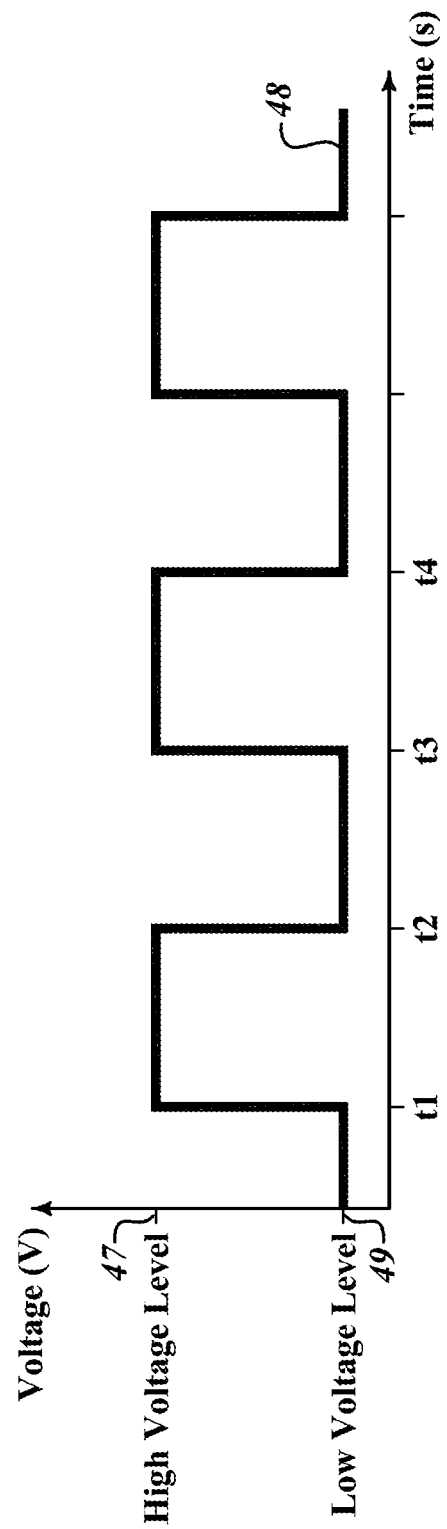
FIG. 5 is a pulse voltage signal according to an embodiment of the present disclosure.

The pulse voltage signal alternates between a first voltage level and a second voltage level that is different from the first voltage level. Stated differently, the pulse voltage signal alternates between a high voltage level and a low voltage level. FIG. 5 is a pulse voltage signal 48 according to an embodiment of the present disclosure. The pulse voltage signal 48 alternates between a high voltage level 47 and a low voltage level 49.

As previously discussed, the heat provided by the heater 24 is proportional to the heating signal received from the power source 16. For example, the heater 24 will heat the gas sensitive material 20 to a high temperature (e.g., 300 degrees Celsius) when the heater 24 receives a high voltage level (e.g., 1.2 volts) from the power source 16, and the heater 24 will no longer heat the gas sensitive material 20 when the heater 24 receives a zero voltage level (e.g., 0 volts) from the power source 16. Accordingly, the heater 24 heats the gas sensitive material 20 to a high temperature when the pulse voltage signal 48 is at the high voltage level 47, and the heater 24 heats the gas sensitive material 20 to a low temperature when the pulse voltage signal 48 is at the low voltage level 49.

In one embodiment, the high voltage level is set to a voltage that will turn the heater 24 on and heat the gas sensitive material 20 to a temperature that causes the gas sensitive material 20 to react with one or more gases. For example, when the gas sensitive material 20 is an SMO film that includes tin dioxide, the high voltage level 47 of the pulse voltage signal 48 is set to a voltage (e.g., 1.2 volts) that will drive the heater 24 to heat the gas sensitive material 20 to 300 degrees Celsius. As a result, the SMO film will react with carbon monoxide and/or ethanol.

In one embodiment, the low voltage level is set to zero volts, to turn the heater 24 off. As a result, the gas sensitive material 20 will no longer be heated and react with gases. For example, when the gas sensitive material 20 is an SMO film that includes tin dioxide, the low voltage level 49 of the pulse voltage signal 48 is set to zero volts, to turn the heater 24 off. As a result, the SMO film will drop to a temperature that is less than 300 degrees Celsius (e.g., room temperature or a temperature of an environment surrounding the gas sensitive material 20), and will no longer react with carbon monoxide and/or ethanol.

In one embodiment, the low voltage level is set to a non-zero voltage that will heat the gas sensitive material 20 to a temperature that will cause the gas sensitive material 20 to not react with one or more gases. For example, if the gas sensitive material 20 is an SMO film that includes tin dioxide, the low voltage level 49 of the pulse voltage signal 48 is set to a voltage (e.g., 0.6 volts) that will drive the heater 24 to heat the gas sensitive material 20 to a temperature lower than 300 degrees Celsius (e.g., 150 degrees Celsius). As a result, the SMO film will no longer react with carbon monoxide and/or ethanol. By heating the gas sensitive material 20 to a low temperature instead of turning the heater 24 off, the gas sensitive material 20 may be heated to a desired temperature faster in a subsequent cycle. For example, if the gas sensitive material 20 is heated to 150 degrees Celsius when the pulse voltage signal 48 is at the low voltage level, the gas sensitive material 20 may be subsequently heated to 300 degrees Celsius (when the pulse voltage signal 48 is at the high voltage level 47) faster than if the gas sensitive material 20 started at room temperature.

Because the pulse voltage signal alternates between a first voltage level (i.e., a high voltage level) and a second voltage level (i.e., a low voltage level), the heater 24 will consume less power, compared to the heater 24 being driven with a constant voltage. As a result, the selective multi-gas sensor device 10 has low power consumption. In one embodiment, as shown for example in FIG. 5, the pulse voltage signal has a 50 percent duty cycle. Stated differently, the pulse voltage signal is at the high voltage level and the low voltage level for equal amounts of time. In one embodiment, the pulse voltage signal is set to the low voltage level for longer periods of time than the high voltage level, to conserve even more power. For example, in one embodiment, the pulse voltage signal has a 20 percent duty cycle with the pulse voltage signal being at the high voltage level for 20 percent of the time and the low voltage level for 80 percent of the time.

In one embodiment, the temperature sensor 22 is used to determine when the gas sensitive material 20 is at a desired temperature. For example, if it is desired to heat the gas sensitive material 20 to 300 degrees Celsius when the pulse voltage signal 48 is at the high voltage level 47, the temperature sensor 22 is used to determine when the gas sensitive material 20 reaches 300 degrees Celsius. In response, the controller 18 may then proceed to block 50 of the method 44. Similarly, if it is desired to have the gas sensitive material 20 at room temperature when the pulse voltage signal 48 is at the low voltage level 49, the temperature sensor 22 is used to determine when the gas sensitive material 20 reaches room temperature. In response, the controller 18 may then proceed to block 54 of the method 44.

As previously discussed, in one embodiment, the gas sensitive material 20 is a thin film. For example, in one embodiment, the gas sensitive material 20 is a thin SMO film that is between 50 nanometers and 150 nanometers thick. By using a thin film for the gas sensitive material 20 as opposed to a thick film (e.g., between 5 micrometers and 20 micrometers thick), the gas sensitive material 20 is able to rapidly heat up or decrease to a target temperature. For example, if the gas sensitive material 20 is an SMO film that includes tin dioxide, the SMO film may be quickly heated to 300 degrees Celsius when the pulse voltage signal 48 is at the high voltage level 47, or quickly cool down (e.g., to room temperature or a temperature of an environment surrounding the gas sensitive material 20) when the pulse voltage signal 48 is at the low voltage level 49.

In block 50, the selective multi-gas sensor device 10 measures a first resistance R1 of the gas sensitive material 20 when the pulse voltage signal has a low voltage level. Namely, the controller 18 instructs the resistance measurement circuit 14 to measure the first resistance R1 of the gas sensitive material 20 while the pulse voltage signal in block 46 is at a low voltage level. For example, referring to FIG. 5, the resistance measurement circuit 14 measures the first resistance R1 of the gas sensitive material 20 when the pulse voltage signal 48 is at the low voltage level 49.

As previously discussed, in one embodiment, the low voltage level of the pulse voltage signal is set to zero volts, to turn off the heater 24. In this embodiment, in block 50, the resistance measurement circuit 14 measures the first resistance R1 of the gas sensitive material 20 while the heater 24 is off and/or when the gas sensitive material is at room temperature (or a temperature of an environment surrounding the gas sensitive material 20).

As previously discussed, in one embodiment, the low voltage level of the pulse voltage signal is set to a non-zero voltage that will heat the gas sensitive material 20 to a temperature that will cause the gas sensitive material 20 to not react with one or more gases (e.g., 150 degrees Celsius). In this embodiment, in block 50, the resistance measurement circuit 14 measures the first resistance R1 of the gas sensitive material 20 when the gas sensitive material 20 is at the temperature that will cause the gas sensitive material 20 to not react with one or more gases.

In block 52, the selective multi-gas sensor device 10 calculates a first sensitivity level S1 of the gas sensitive material 20 using the first resistance R1. Namely, the controller 18 receives the first resistance R1 from the resistance measurement circuit 14, and determines the first sensitivity level S1 of the gas sensitive material 20 based on the first resistance R1.

The first sensitivity level S1 represents a responsiveness level or a change of resistance of the gas sensitive material 20 when the pulse voltage signal in block 46 is at a low voltage level. A large first sensitivity level S1 indicates that the gas sensitive material 20 is highly responsive and undergoes a large change in resistance when the pulse voltage signal in block 46 is at a low voltage level. Conversely, a small first sensitivity level S1 indicates that the gas sensitive material 20 is unresponsive and undergoes a small change in resistance when the pulse voltage signal in block 46 is at a low voltage level. As will be discussed in further detail with respect to blocks 58 and 60, the sensitivity level S1 is used to detect whether a particular gas, such as methane, carbon monoxide, or ethanol, is present.

In one embodiment, the sensitivity level S1 of the gas sensitive material 20 is calculated using equation (1):

$$S1 = \frac{R_{low} - R1}{R_{low}} * 100 \quad (1)$$

R1 is the first resistance measured in block 50. $R_{low}$ is a resistance reference value for the gas sensitive material 20 when the pulse voltage signal in block 46 is at a low voltage level. In one embodiment, $R_{low}$ is a resistance of the gas sensitive material 20 when the gas sensitive material 20 is not exposed to any gas (i.e., is exposed to clean dry air (CDA)) and the heater 24 is supplied with the same low voltage level as in block 50. $R_{low}$ may be determined beforehand by exposing the gas sensitive material 20 to CDA, supplying the low voltage level that is used in block 46 to the heater 24, and measuring a resistance of the gas sensitive material 20 while the heater 24 receives the low voltage level.

As previously discussed, in one embodiment, the low voltage level of the pulse voltage signal is set to zero volts, to turn off the heater 24. In this embodiment, $R_{low}$ is calculated by measuring a resistance of the gas sensitive material 20 when the gas sensitive material 20 is exposed to clean dry air (CDA), and the heater 24 is off and/or the gas sensitive material 20 is at room temperature (or a temperature of an environment surrounding the gas sensitive material 20).

As previously discussed, in one embodiment, the low voltage level of the pulse voltage signal is set to a voltage that will heat the gas sensitive material 20 to a temperature that will cause the gas sensitive material 20 to not react with one or more gases (e.g., 150 degrees Celsius). In this embodiment, $R_{low}$ is calculated by measuring a resistance of the gas sensitive material 20 when the gas sensitive material 20 is exposed to clean dry air (CDA) and the gas sensitive material 20 is at the temperature that will cause the gas sensitive material 20 to not react with one or more gases.

In block 54, the selective multi-gas sensor device 10 measures a second resistance R2 of the gas sensitive material 20 when the pulse voltage signal has a high voltage level. Namely, the controller 18 reads or computes the second resistance R2 of the gas sensitive material 20 via the resistance measurement circuit 14, when the pulse voltage signal in block 46 is at a high voltage level. For example, referring to FIG. 5, the controller 18 determines the second resistance R2 of the gas sensitive material 20 via the resistance measurement circuit 14, when the pulse voltage signal 48 is at the high voltage level 47.

As previously discussed, in one embodiment, the high voltage level of the pulse voltage signal is set to a voltage that will turn the heater 24 on and heat the gas sensitive material 20 to a temperature that causes the gas sensitive material 20 to react with one or more gases (e.g., 300 degrees Celsius). In this embodiment, the resistance measurement circuit 14 measures the second resistance R2 of the gas sensitive material 20 when the gas sensitive material 20 is at the temperature that will cause the gas sensitive material 20 to react with one or more gases.

As previously discussed, in block 50, the selective multi-gas sensor device 10 measures the first resistance R1 of the gas sensitive material 20 when the pulse voltage signal has a low voltage level. In one embodiment, the second resistance R2 is measured in block 54 is during a high voltage level that is immediately adjacent to the low voltage level in block 50. Stated differently, the second resistance R2 is measured during a high voltage level that is immediately preceding or immediately following the low voltage level in block 50. For example, referring to FIG. 5, if the first resistance R1 of the gas sensitive material 20 measured in block 50 is between times t2 and t3, the second resistance R2 is measured in block 54 between times t1 and t2 or between times t3 and t4. By measuring the first resistance R1 and the second resistance R2 in adjacent cycles of the pulse voltage signal, the selective multi-gas sensor device 10 may execute blocks 52, 56, and 58 of the method 44 quicker, obtain more accurate results, and perform gas detection faster.

In block 56, the selective multi-gas sensor device 10 calculates a second sensitivity level S2 of the gas sensitive material 20 using the second resistance R2. Namely, the controller 18 receives the second resistance R2 from the resistance measurement circuit 14, and determines the second sensitivity level S2 of the gas sensitive material 20 based on the second resistance R2.

The second sensitivity level S2 represents a responsiveness level or a change of resistance of the gas sensitive material 20 when the pulse voltage signal in block 46 is at a high voltage level. A large second sensitivity level S2 indicates that the gas sensitive material 20 is highly responsive and undergoes a large change in resistance when the pulse voltage signal in block 46 is at a high voltage level. Conversely, a small second sensitivity level S2 indicates that the gas sensitive material 20 is unresponsive and undergoes a small change in resistance when the pulse voltage signal in block 46 is at a high voltage level. As will be discussed in further detail with respect to block 58, the second sensitivity level S2 is used with the first sensitivity level S1 calculated in block 52 to detect whether a particular gas, such as methane, carbon monoxide, or ethanol, is present.

In one embodiment, the sensitivity level S2 of the gas sensitive material 20 is calculated using equation (2):

$$S2 = \frac{R_{high} - R2}{R_{high}} * 100 \quad (2)$$

R2 is the second resistance measured in block 54. $R_{high}$ is a resistance reference value for the gas sensitive material 20 when the pulse voltage signal in block 46 is at a high voltage level. In one embodiment, $R_{high}$ is a resistance of the gas sensitive material 20 when the gas sensitive material 20 is not exposed to any gas (i.e., is exposed to CDA) and the heater 24 is supplied with the same high voltage level in block 54. $R_{high}$ may be determined beforehand by exposing the gas sensitive material 20 to CDA, supplying the high voltage level that is used in block 46 to the heater 24, and measuring a resistance of the gas sensitive material 20 while the heater 24 receives the high voltage level.

As previously discussed, in one embodiment, the high voltage level of the pulse voltage signal is set to a voltage that will turn the heater 24 on and heat the gas sensitive material 20 to a temperature that causes the gas sensitive material 20 to react with one or more gases (e.g., 300 degrees Celsius). In this embodiment, $R_{high}$ is calculated by measuring a resistance of the gas sensitive material 20 when the gas sensitive material 20 is exposed to CDA and the gas sensitive material 20 is at the temperature that will cause the gas sensitive material 20 to react with one or more gases.

In block 58, the selective multi-gas sensor device 10 calculates a change in sensitivity $S_{change}$ based on the first sensitivity level S1 and the second sensitivity level S2. More specifically, the controller 18 calculates the change in sensitivity $S_{change}$ using the first sensitivity level S1 calculated in block 52 and the second sensitivity level S2 calculated in block 56.

The change in sensitivity $S_{change}$ represents a change in the sensitivity levels of the gas sensitive material 20 when the pulse voltage signal in block 46 switches between a low voltage level and a high voltage level.

In one embodiment, the change in sensitivity $S_{change}$ is calculated using equation (3):

$$S_{change} = \frac{S2}{S1} \quad (3)$$

S1 is the first sensitivity level calculated in block 52. S2 is the second sensitivity level calculated in block 56. Alternatively, one could determine the change in sensitivity based on the difference between S1 and S2.

In block 60, the selective multi-gas sensor device 10 detects a gas based on the change in sensitivity $S_{change}$. More specifically, the controller 18 detects a particular gas using the change in sensitivity $S_{change}$ calculated in block 58. The change in sensitivity $S_{change}$ is used to identify and detect a particular gas by comparing the change in sensitivity $S_{change}$ to a plurality of known change in sensitivities for known gases.

Figure 6:
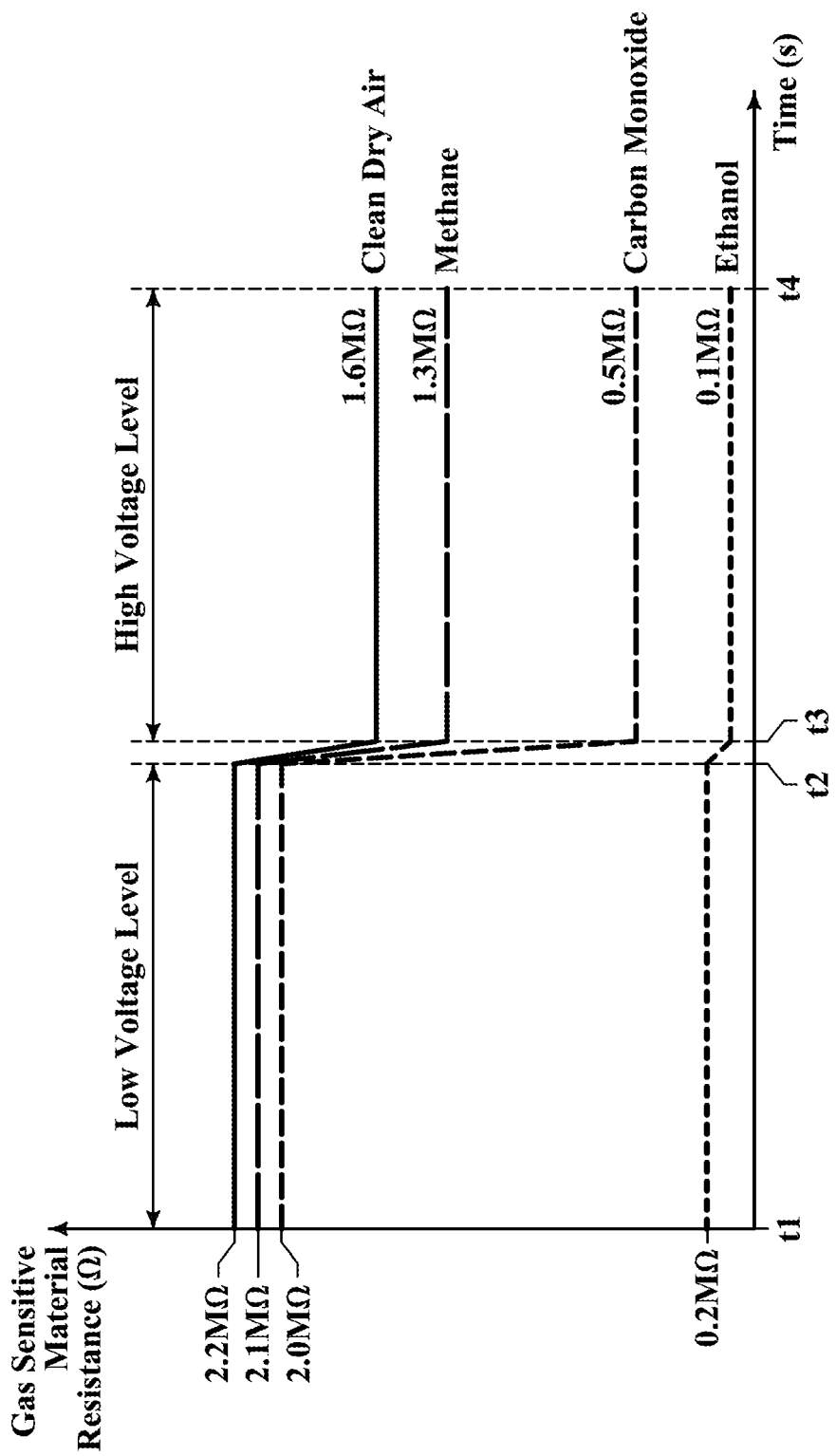
FIG. 6 is a diagram of resistances of a gas sensitive material when exposed to various gases according to an embodiment of the present disclosure.

In one embodiment, a plurality of known change in sensitivities for known gases is calculated beforehand and stored in a lookup table in the controller 18 or a memory coupled to the controller 18. For example, FIG. 6 is a diagram of resistances of the gas sensitive material 20 when exposed to various gases according to an embodiment of the present disclosure. In particular, the resistances shown in FIG. 6 are resistances of the gas sensitive material 20 when the gas sensitive material 20 is exposed to clean dry air, methane, carbon monoxide, and ethanol. The resistances shown in FIG. 6 are measured during the low voltage level and the high voltage level of the pulse voltage signal that is used in block 46.

During the low voltage level (i.e., between times t1 and t2), the gas sensitive material 20 has resistances of 2.2 megaohms, 2.1 megaohms, 2.0 megaohms, and 0.2 megaohms when the gas sensitive material 20 is exposed to clean dry air, methane, carbon monoxide, and ethanol, respectively. Using equation (1), $R_{low}$, is equal to 2.2 megaohms; and the first sensitivity level S1 of the gas sensitive material 20 is approximately equal to 4.55, 9.09, and 90.91 for methane, carbon monoxide, and ethanol, respectively.

During the high voltage level (i.e., between times t3 and t4), the gas sensitive material 20 has resistances of 1.6 megaohms, 1.3 megaohms, 0.5 megaohms, and 0.1 megaohms when the gas sensitive material 20 is exposed to clean dry air, methane, carbon monoxide, and ethanol, respectively. Using equation (2), $R_{low}$, is equal to 2.2 megaohms; and the second sensitivity level S2 of the gas sensitive material 20 is approximately equal to 18.75, 68.75, and 93.75 for methane, carbon monoxide, and ethanol, respectively.

Using equation (3), the change in sensitivities for methane, carbon monoxide, and ethanol is approximately equal to 4.12, 7.56, and 1.03, respectively. The change in sensitivities for methane, carbon monoxide, and ethanol are then stored in a lookup table in the controller 18, or a memory coupled to the controller 18. Table 1 below is an example of a lookup table for the embodiment shown in FIG. 6.

TABLE 1

Lookup table for methane, carbon monoxide, and ethanol.

| Gas | Change in sensitivity |
| --- | --- |
| Methane | 4.12 |
| Carbon monoxide | 7.56 |
| Ethanol | 1.03 |

In one embodiment, the controller 18 compares the calculated change in sensitivity $S_{change}$ in block 58 to the plurality of known change in sensitivities stored in the lookup table, and detects a gas based on differences between the change in sensitivity $S_{change}$ and the plurality of known change in sensitivities in the lookup table. In one embodiment, the controller 18 determines that a particular gas is present if a difference between the change in sensitivity $S_{change}$ and a known change in sensitivities in the lookup table is below a predetermined threshold. For example, using Table 1 and assuming the predetermined threshold is set to 0.5, if the change in sensitivity $S_{change}$ calculated in block 58 is equal to 4, the controller detects methane, as the difference between the change in sensitivity $S_{change}$ and the change in sensitivity of methane is less than the predetermined threshold (i.e., 4.12-4<0.5).

It is noted that multiple gases may be detected in block 60. For example, using Table 1 and assuming the predetermined threshold is set to 2, if the change in sensitivity $S_{change}$ calculated in block 58 is equal to 6, the controller detects methane, as the difference between the change in sensitivity $S_{change}$ and the change in sensitivity of methane is less than the predetermined threshold (i.e., 6-4.12<2), and detects carbon monoxide is present, as the difference between the change in sensitivity $S_{change}$ and the change in sensitivity of methane is less than the predetermined threshold (i.e., 7.56-6<2).

Once a gas has been detected in block 60, the selective multi-gas sensor device 10 may perform various actions in response. For example, the selective multi-gas sensor device 10 may alert a user with a light or an alarm, and/or transmit the identity of the detected gas to an external device for further processing.

In one embodiment, if no gas is detected in block 60 (e.g., none of the differences between the change in sensitivity $S_{change}$ and the plurality of known change in sensitivities in the lookup table are below a predetermined threshold), the method 44 returns to block 46.

It is noted that the blocks of the method 44 shown in FIG. 4 may be performed in various different orders. For example, blocks 50 and 52 may be performed concurrently with blocks 54 and 56, blocks 50 and 52 may be performed prior to blocks 54 and 56, blocks 50 and 52 may be performed subsequently to blocks 54 and 56, and blocks 50 and 54 may be performed prior to block 52 and/or block 56.

The various embodiments provide a selective multi-gas sensor device, and a method for selectively detecting multiple gases based on a ratio between a sensitivity of the gas sensitive material when the heater is turned on and a sensitivity of the gas sensitive material when the heater is turned off.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
supplying a heating signal to a heater of a gas sensor, the heating signal alternating between a first level and a second level that is greater than the first level, the heater configured to heat a gas sensitive material of the gas sensor in response to receiving the heating signal;
measuring a first resistance of the gas sensitive material when the heating signal is at the first level;
measuring a second resistance of the gas sensitive material when the heating signal is at the second level;
detecting a gas surrounding the gas sensor based on the first resistance of the gas sensitive material and the second resistance of the gas sensitive material;
measuring a third resistance of the gas sensitive material when the heating signal is at the first level;
measuring a fourth resistance of the gas sensitive material when the heating signal is at the second level; and
detecting another gas surrounding the gas sensor based on the third resistance of the gas sensitive material and the fourth resistance of the gas sensitive material.

2. The method of claim 1, further comprising:
calculating a first sensitivity level of the gas sensitive material based on the first resistance and a first reference sensitivity level; and
calculating a second sensitivity level of the gas sensitive material based on the second resistance and a second reference sensitivity level.

3. The method of claim 2 wherein the detecting includes detecting the gas surrounding the gas sensor based on the first sensitivity level and the second sensitivity level.

4. The method of claim 2 wherein the detecting includes detecting the gas surrounding the gas sensor based on a ratio between the first sensitivity level and the second sensitivity level.

5. The method of claim 1, further comprising:
heating the gas sensitive material to a first temperature when the heating signal is at the first level; and
heating the gas sensitive material to a second temperature when the heating signal is at the second level, the second temperature being different from the first temperature.

6. The method of claim 1 wherein the gas sensitive material is a semiconductor metal oxide.

7. The method of claim 1 wherein the first level is zero volts.

8. A device, comprising:
a gas sensor including a gas sensitive material and a heater;
a power source configured to supply a heating signal to the heater, the heating signal alternating between a first level and a second level that is greater than the first level, the heater configured to heat the gas sensitive material in response to receiving the heating signal;
a resistance measurement circuit configured to:
measure a first resistance of the gas sensitive material when the heating signal is at the first level;
measure a second resistance of the gas sensitive material when the heating signal is at the second level;
measure a third resistance of the gas sensitive material when the heating signal is at the first level; and
measure a fourth resistance of the gas sensitive material when the heating signal is at the second level; and
a processor configured to detect a gas surrounding the gas sensor based on the first resistance of the gas sensitive material and the second resistance of the gas sensitive material, and detect another gas surrounding the gas sensor based on the third resistance of the gas sensitive material and the fourth resistance of the gas sensitive material.

9. The device of claim 8 wherein the processor is configured to calculate a first sensitivity level of the gas sensitive material based on the first resistance and a first reference sensitivity level, and calculate a second sensitivity level of the gas sensitive material based on the second resistance and a second reference sensitivity level.

10. The device of claim 9 wherein the processor is configured to detect the gas surrounding the gas sensor based on a ratio between the first sensitivity level and the second sensitivity level.

11. The device of claim 8 wherein the gas sensor includes a cavity that directly underlies the gas sensitive material.

12. The device of claim 8 wherein the gas sensitive material is a semiconductor metal oxide.

13. The device of claim 12 wherein the gas sensitive material has a thickness between 50 nanometers and 150 nanometers.

14. A method, comprising:
heating a gas sensitive material of a gas sensor to a first temperature;
measuring a first resistance of the gas sensitive material in response to detecting that the gas sensitive material is at the first temperature;
heating the gas sensitive material to a second temperature that is greater than the first temperature;
measuring a second resistance of the gas sensitive material in response to detecting that the gas sensitive material is at the second temperature;
detecting a gas surrounding the gas sensor based on the first resistance of the gas sensitive material and the second resistance of the gas sensitive material;
measuring a third resistance of the gas sensitive material in response to detecting that the gas sensitive material is at the first temperature;
measuring a fourth resistance of the gas sensitive material in response to detecting that the gas sensitive material is at the second temperature; and
detecting another gas surrounding the gas sensor based on the first resistance of the gas sensitive material and the second resistance of the gas sensitive material.

15. The method of claim 14, further comprising:
calculating a first sensitivity level of the gas sensitive material based on the first resistance and a first reference sensitivity level; and
calculating a second sensitivity level of the gas sensitive material based on the second resistance and a second reference sensitivity level.

16. The method of claim 15 wherein the first reference sensitivity level is a resistance of the gas sensitive material when the gas sensitive material is at the first temperature and exposed to clean dry air, and the second reference sensitivity level is a resistance of the gas sensitive material when the gas sensitive material is at the second temperature and exposed to clean dry air.

17. The method of claim 15 wherein the gas surrounding the gas sensor is detected based on a ratio between the first sensitivity level and the second sensitivity level.

18. The method of claim 14 wherein the first temperature is a temperature of an environment surrounding the gas sensor.

19. The method of claim 14 wherein the gas sensitive material is a semiconductor metal oxide.

\* \* \* \* \*

UNITED STATES PATENT AND TRADEMARK OFFICE
CERTIFICATE OF CORRECTION

| | | |
|---|---|---|
| PATENT NO. | : 11,774,422 B2 | Page 1 of 1 |
| APPLICATION NO. | : 16/458561 | |
| DATED | : October 3, 2023 | |
| INVENTOR(S) | : Fangxing Yuan et al. | |

It is certified that error appears in the above-identified patent and that said Letters Patent is hereby corrected as shown below:

On the Title Page

Item (56) References Cited, Please correct to read:

--US PATENT DOCUMENTS:

5,298,783 A    3/1994    Wu

FOREIGN PATENT DOCUMENTS:

JP    2000275202    A    10/2000
JP    2017138191    A    08/2017
JP    2018205105    A    12/2018--

Signed and Sealed this
Twenty-seventh Day of May, 2025

Coke Morgan Stewart
*Acting Director of the United States Patent and Trademark Office*